(12) United States Patent
Kitzer (10) Patent No.: US 8,834,986 B2
(45) Date of Patent: Sep. 16, 2014

(54) CONTINUOUS WEB OF A PLURALITY OF TABS AND METHODS OF MAKING AND USING THE SAME

(75) Inventor: Peter Kitzer, Echt (NL)

(73) Assignee: 3M Innovative Properties Company, St. Paul, MN (US)

( * ) Notice: Subject to any disclaimer, the term of this patent is extended or adjusted under 35 U.S.C. 154(b) by 600 days.

(21) Appl. No.: 13/028,874

(22) Filed: Feb. 16, 2011

(65) Prior Publication Data

US 2012/0205037 A1    Aug. 16, 2012

(51) Int. Cl.
  *B32B 3/24*    (2006.01)
  *B31D 1/00*    (2006.01)
  *A61F 13/15*    (2006.01)

(52) U.S. Cl.
  CPC ........ *A61F 13/15723* (2013.01); *B31D 1/0062* (2013.01); *A61F 13/15756* (2013.01)
  USPC .............. 428/136; 428/135; 156/250; 156/60

(58) Field of Classification Search
  USPC .............................. 428/136, 135; 156/250, 60
  See application file for complete search history.

(56) References Cited

U.S. PATENT DOCUMENTS

| | | |
|---|---|---|
| 4,001,366 A | 1/1977 | Brumlik |
| 4,061,527 A | 12/1977 | Traise |
| 5,464,497 A | 11/1995 | Unthank |
| 5,759,340 A | 6/1998 | Boothe et al. |
| 6,017,406 A | 1/2000 | Vogt |
| 6,146,369 A | 11/2000 | Hartman |
| 6,350,339 B1 | 2/2002 | Sessions |
| 7,005,027 B2 | 2/2006 | Valenti |
| 7,875,012 B2 | 1/2011 | Arco |
| 8,020,262 B2 | 9/2011 | Oertel |
| 2002/0152860 A1 | 10/2002 | Machamer |
| 2003/0008106 A1 | 1/2003 | Guenther |
| 2003/0130644 A1 | 7/2003 | Baker |
| 2004/0170801 A1 | 9/2004 | Seth |
| 2005/0101929 A1 | 5/2005 | Waksmundzki |
| 2005/0113791 A1 | 5/2005 | Neubauer |

(Continued)

FOREIGN PATENT DOCUMENTS

| | | |
|---|---|---|
| EP | 0191355 | 8/1986 |
| EP | 0597609 | 5/1994 |
| WO | WO 94/02091 | 2/1994 |
| WO | WO 2006/071434 | 7/2006 |

OTHER PUBLICATIONS

International Search Report from International Application No. PCT/US2012/025408, filing date Feb. 16, 2012.

*Primary Examiner* — William P Watkins, III (57) ABSTRACT

An elongate continuous material web is disclosed that includes a plurality of adjacent tabs arranged in a longitudinal direction of the web with connection regions between adjacent tabs. Each connection region includes three or more incisions that extend in the transverse direction of the web and are arranged in a manner such that at least one extensible connection member, extensible in the longitudinal direction of the web, is formed. At least one incision forms a side incision that travels through one longitudinal edge of the web, and at least one incision forms a further side incision that travels through the other longitudinal edge of the web. Also disclosed are a method for making such a web, a method for manufacturing a tab from such a web, a method for manufacturing an absorbent hygiene product with the help of such a web, and a cutting device to produce such a web.

21 Claims, 7 Drawing Sheets

(56) References Cited

U.S. PATENT DOCUMENTS

| | | | |
|---|---|---|---|
| 2005/0136215 A1* | 6/2005 | Kuchar | ................. 428/136 |
| 2005/0271858 A1 | 12/2005 | Ausen | |
| 2007/0039142 A1 | 2/2007 | Petersen | |
| 2007/0151660 A1 | 7/2007 | Adams | |
| 2007/0157778 A1 | 7/2007 | Lohrengel et al. | |
| 2007/0181247 A1 | 8/2007 | Adams | |
| 2008/0135161 A1 | 6/2008 | Bohanan | |
| 2008/0236733 A1 | 10/2008 | Hudetz | |
| 2011/0313389 A1 | 12/2011 | Wood | |
| 2012/0204383 A1 | 8/2012 | Wood | |

\* cited by examiner

# CONTINUOUS WEB OF A PLURALITY OF TABS AND METHODS OF MAKING AND USING THE SAME

BACKGROUND

It is a common technique to provide diapers or feminine hygiene articles with fastening tabs. Such fastening tabs allow an adjustable connection of different areas of the diaper or the hygiene article in order to ensure a firm and comfortable fit at the human body. For this purpose, the fastening tabs are usually provided with an adherent layer, e.g., in the form of a hook-and-loop fastener, a pressure sensitive adhesive layer or the like.

During the fabrication of such hygiene products, the tab material is usually provided as a continuous material web, which is subsequently cut into singular tabs. In the next step, these tabs are spacially separated from each other and adhered to desired areas of the hygiene product raw material.

It is always desirable to increase the production velocity of such hygiene articles as far as possible. However, the handling of the tabs is a limiting factor in that context. It is a known problem that the lightweight fastening tabs may fly around in the machinery as soon as the rotation velocity of the transportation cylinders becomes too high, due to the airflow caused by the rotation. This may lead to malfunction of the machinery as well as missing or incorrectly positioned fastening tabs on the hygiene products, in other words, it may lead to production loss.

To overcome these problems, it is known from U.S. Pat. No. 4,061,527 (Traise) to transport the individually cut fastening tabs immediately after cutting to a vacuum cylinder from which they are positioned on the diaper raw material. However, vacuum cylinders are very expensive. Moreover, they are not adapted for properly receiving all forms or structures of fastening tabs, especially tabs having a rough structured surface, like hook tabs. In addition, the transportation of tabs covered with a pressure sensitive adhesive on both sides might is also very problematic, because the tabs stick to the vacuum cylinder and are difficult to remove.

SUMMARY

The present disclosure describes providing fastening tabs from a continuous material web at high production speed without causing the above mentioned problems. The type of tab to be processed should not be limited in the above mentioned way.

The present disclosure relates to an elongate continuous material web comprising a plurality of adjacent tabs arranged in a longitudinal direction of the web, wherein connection regions are provided between adjacent tabs and said connection regions comprise incisions that extend in a transverse direction of the web. The disclosure is further directed to a method for manufacturing a tab from such a web, especially a fastening tape tab, a hook tab or the like, which may be particularly used for diapers or feminine hygiene articles as a mechanical closure component. Moreover, the present disclosure relates to a cutting device for the fabrication of an elongate continuous material web.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

According to the present disclosure, the aforementioned problems are solved by an elongate continuous material web comprising a plurality of adjacent tabs arranged in a longitudinal direction of the web, wherein connection regions being provided between adjacent tabs comprising incisions that extend in a transverse direction of the web, wherein each connection region comprises three or more incisions that extend in the transverse direction of the web and are arranged in such a manner that at least one extensible connection member is formed that is extensible in the longitudinal direction of the web, wherein at least one incision forms a side incision that travels through one longitudinal edge of the web, and at least one incision forms a further side incision that travels through the other longitudinal edge of the web.

The development of such a web is based on the recognition that adjacent tabs may be arranged and spaced apart from each other by connection regions interposed between two adjacent tabs. The connection regions have extensible connection members so that the tabs are interconnected in a chain-like manner. The arrangement of the incisions typically leads to a meander-like shape of each of the connection members.

The extensible properties are provided by the meander-like shape of the extensible connection members. Accordingly, adjacent tabs can be separated from each other in the longitudinal direction of the web until the meander-like shape is fully stretched. Thus, the length of the meander-like structure of the shortest extensible connection member defines the maximum separation of adjacent tabs. Those incisions of an extensible connection member which travel substantially widthwise across the web are usually parallel to each other although the incisions might be arranged slightly angled to each other as well.

To produce such an elongate continuous material web a method may be applied which comprises the steps of forming each connection region by arranging three or more incisions that extend in the transverse direction of the web in such a manner that at least one extensible connection member is formed that is extensible in the longitudinal direction of the web, wherein at least one incision forms a side incision that travels through one longitudinal edge of the web, and at least one incision forms a further side incision that travels through the other longitudinal edge of the web.

The web according to the current disclosure may specifically be realized by that at least one of the connection regions consists of one single connection member that comprises at least three adjacent incisions, each travelling through one longitudinal edge of the web to almost the opposing longitudinal edge in alternating manner.

According to another embodiment of this disclosure, at least one of the connection regions consists of two connection members, arranged side by side in the transverse direction of the web, and separated from each other by a separating incision that extends in the lengthwise direction of the web, wherein each extensible connection member comprises at least and in particular exactly three incisions which extend in alternating manner from the separating incision to almost one longitudinal edge of the web and through said longitudinal edge to almost the separating incision, wherein especially the side incisions are embraced by the other incisions, if an uneven number of incisions is present in the connection member, respectively. Such an embodiment has the advantage that two adjacent tabs are connected to each other at least two areas, respectively, so that when the extensible connection members are formed to provide the same length, the tabs are parallely spaced apart, if the extensible connection members are stretched to their full extent. The separating incisions may travel parallel to the longitudinal direction of the web, but as well at any other angle.

Such a parallel spacing of tabs may be achieved, if the extensible connection members between each pair of adjacent tabs are provided in mirror-symmetrical or point-symmetrical manner.

In the embodiment, according to which at least one of the connection regions consists of two connection members, these two connection members may be in alignment with each other. However, it may also be desired that the two connection members are arranged to each other in an angled manner, for example to provide angled tabs after the connection members have been removed. Such an arrangement of connection members is especially useful with even numbers of connection members per connection region.

Besides the possibilities presented above, in which a connection region may consist of one or two extensible connection members arranged between two adjacent tabs, also three, four or even more extensible connection members may be arranged between two adjacent tabs. It is also possible that one web comprises different connection regions with different numbers of connection members each.

Hence, according to another embodiment, at least one of the connection regions consists of three extensible connection members, arranged side by side in the transverse direction of the web, wherein the inner extensible connection member is separated from the outer extensible connection members by separating incisions that extend in the lengthwise direction of the web, and the incisions of the inner extensible connection member extend from one of the separating incisions to almost the other in alternating manner, and wherein the outer extensible connection members comprise at least three or more adjacent incisions which extend in alternating manner from the separating incisions to almost one longitudinal edge of the web and through said edge to almost the separating incisions, respectively, whereas especially the side incisions are embraced by the other incisions, if an uneven number of incisions is present in the connection member, respectively.

It is further preferred that the incisions of each extensible connection member are uniformly spaced from one another. This results in a homogeneous stretching stability of the connection members because the uniform spacing leads to uniform widths of the connection members.

Although the incisions may extend across the web in any desired angle, it may be desirous that the incisions extend mostly perpendicular to the longitudinal direction of the web. This results to uniformly stretchable connection regions and rectangular tabs after removal of the connection members.

A preferred embodiment of the web is where each extensible connection member is formed by an uneven number of adjacent incisions. An uneven number of incisions prevents an axial misalignment of adjacent tabs upon extension of the extensible connection members in the longitudinal direction.

To ensure that two adjacent tabs may be spaced apart parallely upon extension of the extensible connection members, each extensible connection member between two adjacent tabs may be formed by the same number of adjacent incisions. Preferably, the spacings between these incisions are identical as well.

According to another preferred embodiment of the web according to the present disclosure, at least one of the incisions, preferably at least one of the adjacent incisions and/or the separating incisions is provided with a hole punching at its end region. The separating incisions can be provided with such hole punchings as well. The hole punchings may be of oval or circular shape, for example, and facilitate the stretching of the meander-like shaped extensible connection members because of their hinge-like functionality. In addition, the punching holes prevent tearing of the incisions if a pull force is applied to the meander-like shaped extensible connection members.

Although typically all tabs and connection members of a web of this disclosure have the same appearance over the whole length of the web, it is also possible and sometimes desirable to provide differently shaped tabs and/or connection members in one single web. This may be the case, if, for example, two differently shaped tabs are needed as fastening means for a diaper. In this case, the two differently shaped tabs can be arranged in sequenced repeating units in the web.

The web according to the present disclosure may comprise numerous types of material, especially those which are suitable to be used as material for fastening tabs. These materials are preferably chosen from polymers, metals, paper or card board or combinations thereof. Polymers which are especially suitable are chosen from the group comprising polyolefins, like polyethylene or polypropylene, polyamides, polyurethanes, polyesters, polyethers, biodegradable polymers, like polylactic acid, polybutylenesuccinate, polyhydroxyalkanoates, polytrimethyleneterephthalate, starch- or starch derivate-based polymers, or mixtures thereof. These materials are only examples and not to be understood in a limiting manner. The materials can be used as film or in other forms, for example laminates of woven or nonwoven webs with elastic or non-elastic films.

It is further preferred that the web according to the present disclosure is at least on one main surface at least partly provided with an adherent agent, especially chosen from hooks, loops, adhesives or mixtures thereof.

It is further preferred that, if both main surfaces are provided with an adherent agent, one of those is an adhesive, especially a pressure sensitive adhesive. The surface covered with an adhesive may be used to attach the tab on the raw material of the hygiene product.

In principle, all kinds of adhesives can possibly be used in the scope of the present disclosure, whereas pressure sensitive adhesives are preferred and may be especially chosen from the group comprising acrylate-based, styrl-copolymer-based, rubber-based adhesives or mixtures thereof.

In some applications it may be desirable to remove the connection members from the tabs to give discrete patches of fastening material for example. In order to allow simple removal of the connection members from the neighboring tabs especially after the tabs have been attached to a desired surface area of a hygiene product, the web may be provided on one or both of its long sides with a line of weakness, especially a perforation, extending in the longitudinal direction and travelling in such a way through the extensible connection members that if the line of weakness is broken, the extensible connection members are separated from their assigned tabs. Such an embodiment is especially preferred if the adjacent tabs of the web are connected by one or two extensible connection members, located at the long sides of the web.

To produce such a line of weakness, it is possible to provide them at any time during the production of the elongate continuous material web, for example at the same time as the connection member incisions are made. However, it is possible as well to provide the lines of weakness during or after the tabs of the web have been attached to a desired surface area of a hygiene product. This allows easy removal of the extensible connection members from the tabs and provides smooth side edges on the long sides of the tabs.

The web according to the present disclosure may be directly used to attach tabs to hygiene material to produce diapers or female hygiene articles. However, it is also possible to wind such a continuous material web on a roll to be used later or to be transported or sold as an intermediate product for the production of hygiene articles later.

Another aspect of this disclosure is an elongate continuous material web comprising a plurality of adjacent tabs arranged in a longitudinal direction of the web, whereas between two tabs at least one hole is present, whereas the holes are formed by extending a continuous material web as described above in its longitudinal direction. Hence, this disclosure provides an elegant way how a web with holes can be provided without material loss by punching the holes directly into the material web. The width of the holes can be modified by altering the widths of the connection members. As an example, smaller holes can be produced if the incisions of the meander-like cuttings are further spaced apart. Typical widths of incision spacing, i.e. widths of the connection members, are from about 0.5 to 20 mm, preferably about 1 to 10 mm.

The length of the holes is almost not affected by the width of the connection members. To alter the length of the holes, the number of connection members per connection region may be increased.

In that context, the form of the holes can be modified by arranging the incisions of one connection region in an angled manner as described above. This may lead to arrowed holes for example.

A further aspect of the present disclosure is directed to a method for producing an elongate continuous material web comprising a plurality of adjacent tabs arranged in a longitudinal direction of the web and connection regions being provided between adjacent tabs comprising incisions that extend in a transverse direction of the web, whereas the method comprises the steps of forming each connection region by arranging three or more incisions that extend in the transverse direction of the web in such a manner that at least one extensible connection member is formed that is extensible in the longitudinal direction of the web, and wherein the connection region is further provided with a side incision at both opposing edges of the long sides of the web, which travels through the edge.

The removal of the connection regions or the connection members, respectively, can be carried out in different manners. One possibility is to prepare lines of weakness and to remove the edge areas along these lines as explained above. Another way is to cut away these edge areas after or while the tabs are attached.

Another aspect of the present disclosure is a method for manufacturing an absorbent hygiene or sanitary product, especially a diaper or a sanitary napkin, the method comprising the steps of providing an elongate absorbent hygiene material web or prepared portions thereof, providing a continuous material web as described above, bringing the continuous material web into contact with the elongate absorbent hygiene material web in such a way that its tabs are positioned at desired locations of the elongate absorbent hygiene material web, attaching the tabs at those areas and, at the same time or thereafter, optionally removing at least the connection members between the tabs.

This production method is especially advantageous because it allows the pre-preparation of singular tabs attached to each other in a chain-like manner from which they may be adhered to the surface of a hygiene product raw material. In other words, according to this production method, the tabs are separated from the elongate continuous material web during or after they have been attached to a surface so that they cannot fly around in the production machinery.

In that method for manufacturing an absorbent hygiene or sanitary product, it is further preferred that before or simultaneously with the step of bringing the continuous material web into contact with the elongate absorbent hygiene material web, the feed velocity of the continuous material web is increased so that the extensible connection members are stretched, preferably mostly fully stretched. This stretching leads to spacings between the tab areas and allows easier positioning, especially if the connection members are fully stretched, because this leads to defined spaces between the tabs. This embodiment may be realized by transporting the continuous material web over at least two rotating cylinders, from which that cylinder which is located downstream has a higher rotation velocity compared to the upstream cylinder. The velocity gradient between these two cylinders may be adjusted in such a way that the extensible connection members are stretched as far as it is desired.

A further aspect of the present disclosure is a cutting device, especially in the form of a cutting cylinder, for the fabrication of a continuous material web comprising a plurality of adjacent tabs arranged in a longitudinal direction of the web, wherein connection regions being provided between adjacent tabs comprising incisions that extend in a transverse direction of the web, whereas the cutting device comprises groups of cutting members (e.g., blades and/or punching units), arranged in such a way as to form each connection region by three or more incisions that extend in the transverse direction of the web and are arranged in such a manner that at least one extensible connection member is formed that is extensible in the longitudinal direction of the web, wherein said cutting members (e.g., blades and/or punching units) are arranged to provide at least one incision which forms a side incision that travels through one longitudinal edge of the web, and at least one incision which forms a further side incision that travels through the other longitudinal edge of the web.

The present disclosure is however not limited to the field of use connected to hygiene or sanitary products but may generally be used in other processes, where discrete components, such as labels for example, are to be applied to a continuous web.

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

Figure 1:
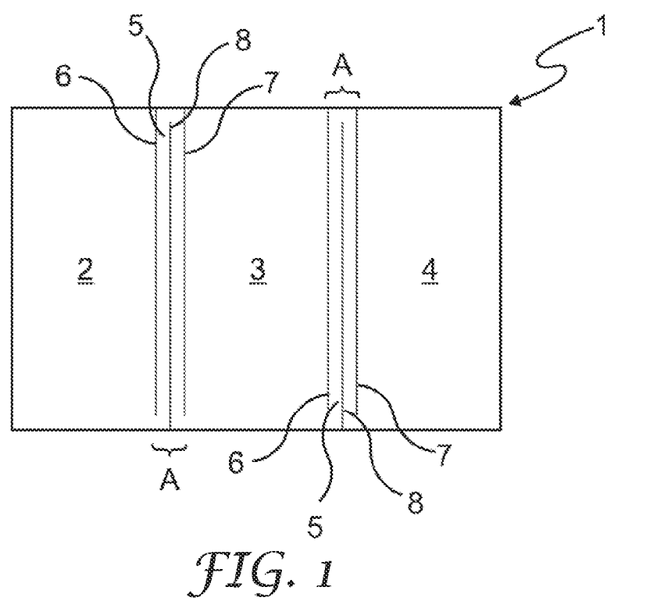
FIG. 1 shows a first embodiment of an elongate continuous material web with one extensible connection member between two adjacent tabs.

In FIG. 1, an example section of an elongate continuous material web 1 is shown, which comprises a plurality of adjacent tabs 2, 3, 4 arranged in a longitudinal direction of the web 1. The web 1 is made of bi-axially oriented polypropylene (PP) provided with hooks on a first major surface and a pressure sensitive adhesive layer on the opposing main surface.

Each of the tabs 2, 3, 4 is connected to its adjacent tab 2, 3, 4 by a connection region A, which consists of one meander-like shaped extensible connection member 5. The extensible connection member 5 is formed by three adjacent incisions 6, 7, 8 laterally arranged to the longitudinal direction of the web 1. Each of the incisions 6, 7, 8 extend through one longitudinal edge of the web 1 to almost the opposing longitudinal edge in alternating manner. Accordingly, the outer incisions (6, 7) travel through one edge of the long sides of the web 1, whereas the middle incision 8 travels through the opposing edge of the long sides of the web 1. Thus, the incisions 6, 7, 8 represent side incisions.

Figure 2:
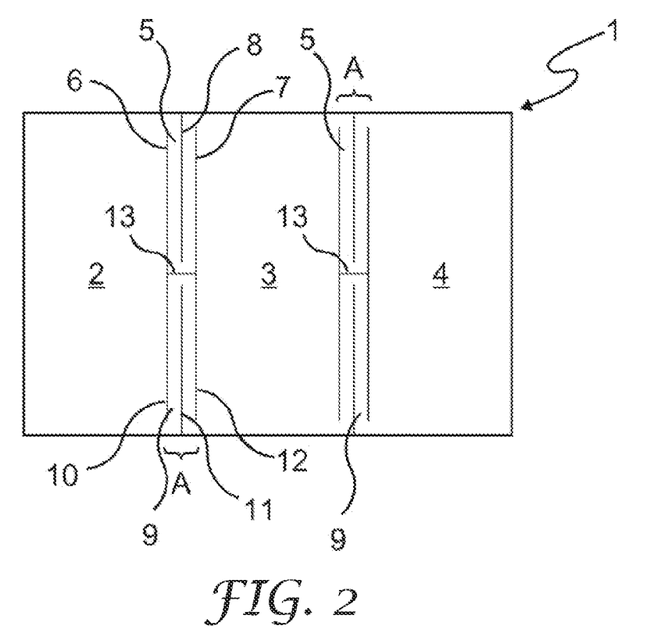
FIG. 2 shows a second embodiment of the web with two extensible connection members between two adjacent tabs.

FIG. 2 shows an alternative embodiment of an elongate continuous material web 1 in which each of the adjacent tabs 2, 3, 4 is separated from its neighbor by two meander-like shaped extensible connection members 5, 9, both representing a connection region A. Each of the extensible connection members 5, 9 is formed by three adjacent incisions 6, 7, 8, 10, 11, 12, whereas the extensible connection members are separated from one another by a separating incisions 13, in the current case parallel to the longitudinal direction of the web 1. Both outermost extensible connection members 5, 9 comprise one side incision 8, 11, each.

Figure 3:
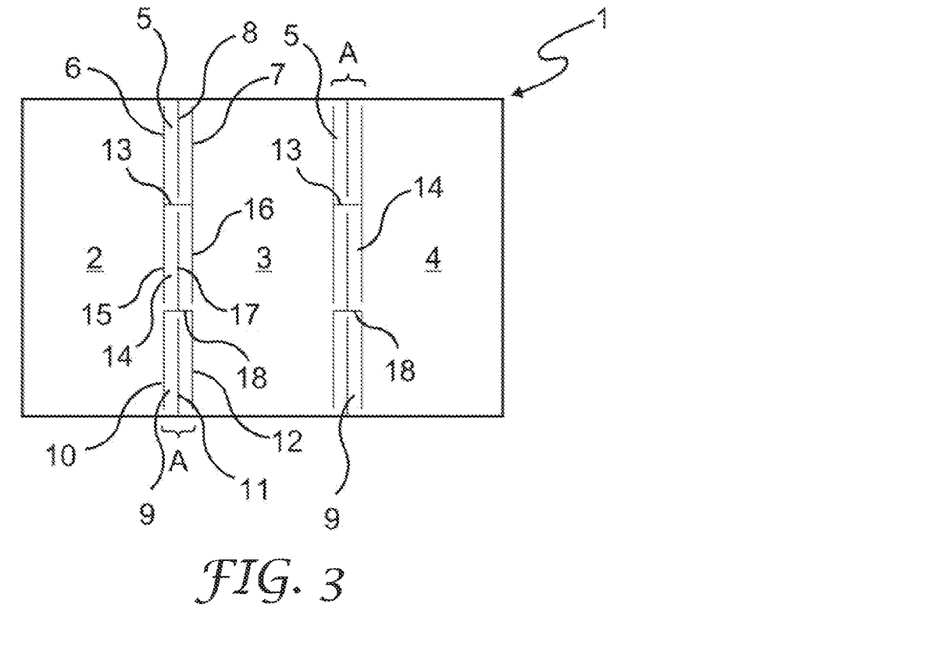
FIG. 3 shows a third embodiment with three extensible connection members between two adjacent tabs.

FIG. 3 presents another embodiment of an elongate continuous material web 1 according to the present disclosure, in which each of the tabs 2, 3, 4 is connected to its adjacent tab by a connection region A, which consists of three meander-like shaped extensible connection members 5, 9, 14, respectively. Each of the extensible members 5, 9, 14 is composed out of three adjacent incisions 6, 7, 8, 10, 11, 12, 15, 16, 17, from which both outermost extensible connection members 5, 9 comprise one side incision 8, 11, each. The extensible connection members 5, 9, 14 are separated from each other by separating incisions 13, 18, travelling parallel the longitudinal direction of the web.

Figure 4:
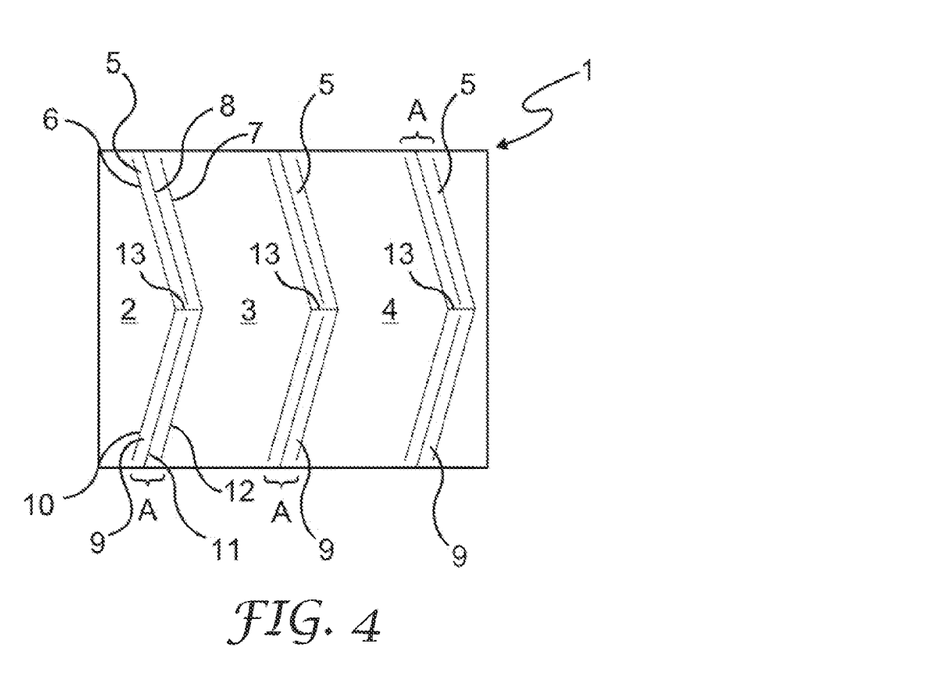
FIG. 4 shows a forth embodiment of the web with two extensible connection members arranged angled between two adjacent tabs.

In FIG. 4, an alternative embodiment to that one shown in FIG. 2 is presented which differs insofar that each of the two extensible connection members 5, 9 interposed between adjacent tabs 2, 3, 4 are not in alignment with one another but are arranged in an angled manner. This leads to angled-shaped tabs 2, 3, 4.

Figure 5:
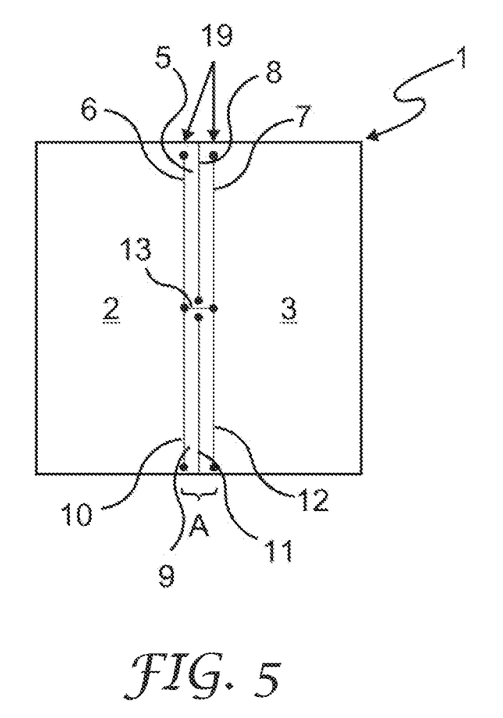
FIG. 5 shows a web with hole punchings at end regions of adjacent incisions.

In FIG. 5, a further alternative embodiment of the elongate continuous material web 1 is shown. The constitution of the web 1 is similar to that one presented in FIG. 2 with the difference that the incisions 6, 7, 8, 10, 11, 12 as well as the side incision 13 are provided with hole punchings 19 at one of their end regions. The hole punchings 19 work as hinges if the extensible connection members 5, 9 are exposed to a stretching force in the longitudinal direction of the web 1. In addition, the punching holes 19 prevent tearing of the extensible connection members in the areas, where the punching holes 19 are applied.

Figure 6A:
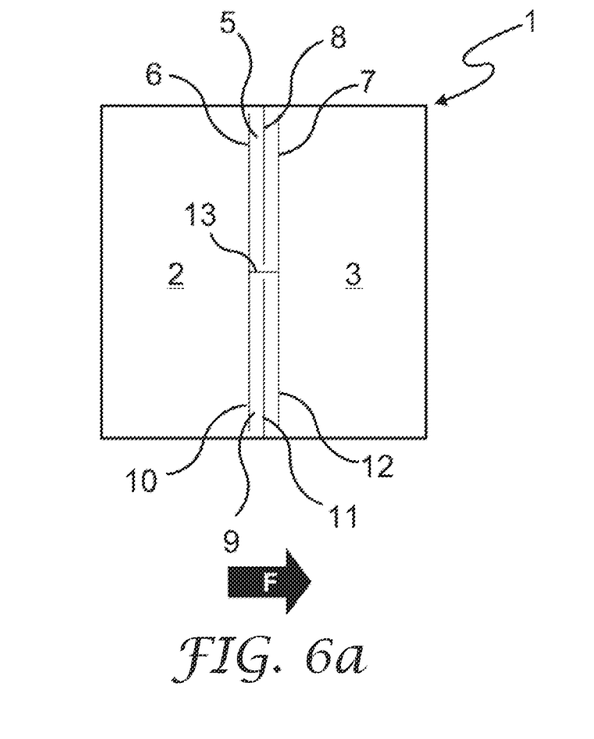
FIGS. 6a to 6c show the web according to FIG. 2 upon application of a pull force in longitudinal direction as a flow chart.
Figure 6B:
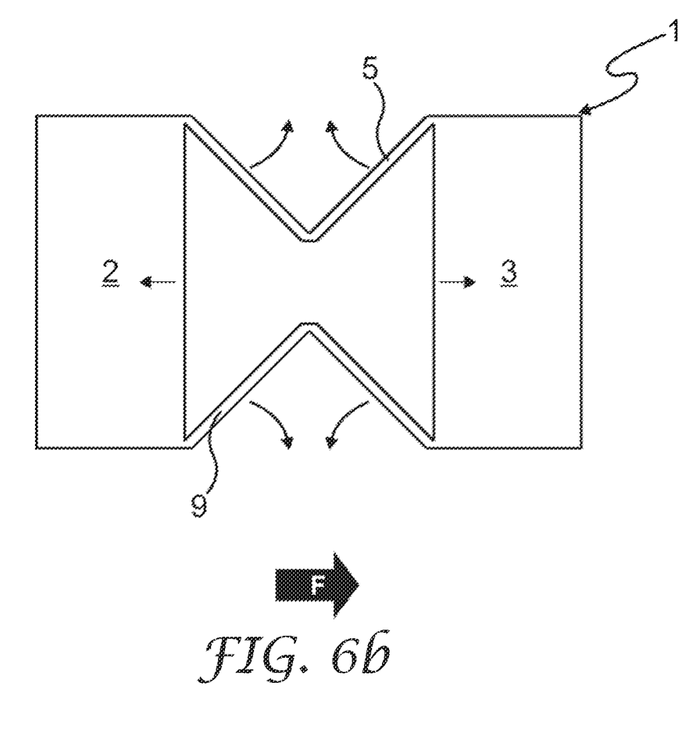
Figure 6C:
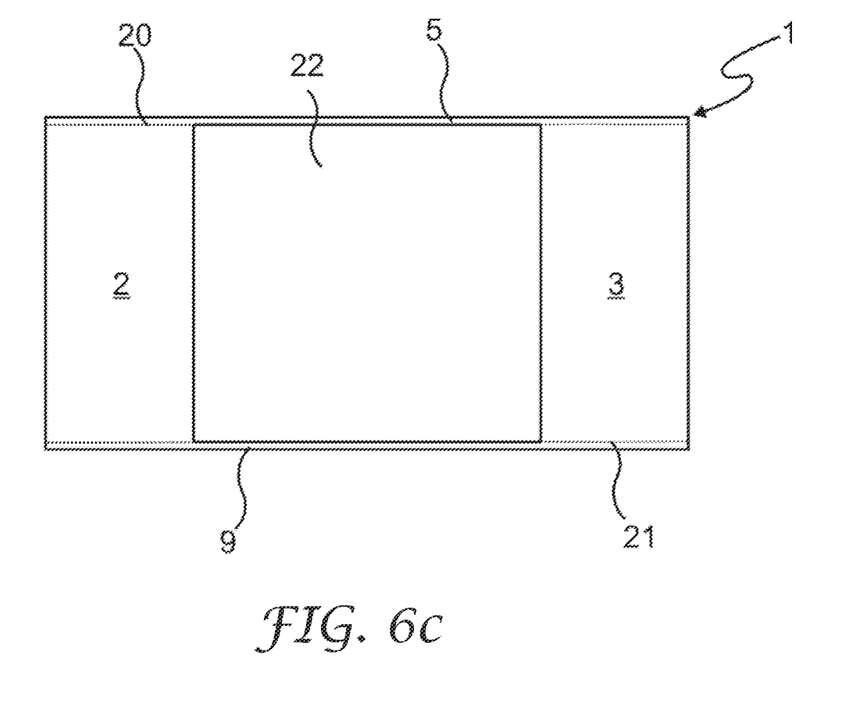

FIGS. 6a to 6c represent a flow chart of the separation of the tabs 2, 3 from an elongate continuous material web 1 according to FIG. 2. According to FIG. 6a, the adjacent tabs 2, 3 are connected to each other by two meander-like shaped extensible connection members 5, 9 from which each one comprises a side incision 8, 11.

FIG. 6b shows the behavior of the web 1 upon subjecting it to a pull force F parallel to the longitudinal direction of the web 1, indicated with a black arrow. The tabs 2, 3 are spaced apart from each other as signified by arrows in the tabs 2, 3. At the same time, the extensible connection members 5, 9 swing outwardly as indicated by bent arrows. However, this presentation is in so far idealized as the extensible connection members 5, 9 are as well bent out of the plain area, defined by the web 1.

In FIG. 6c, the extensible connection members 5, 9 are fully stretched to give the adjacent tabs 2, 3 a defined spacing. The stretching leads also to the formation of a hole 22 between the adjacent tabs.

At this stage, lines of weakness 20, 21 in the form of perforation lines are applied in alignment with the extensible connection members 5, 9. However, it is also possible to prepare the perforation lines 20, 21 at the same time as the connection member incisions 6, 7, 8, 10, 11, 12 are made. When the perforation lines 20, 21 are torn, the extensible connection members 5, 9 as well as slender edge areas from the tabs 2, 3 are removed to yield single tabs 2, 3.

Figure 7A:
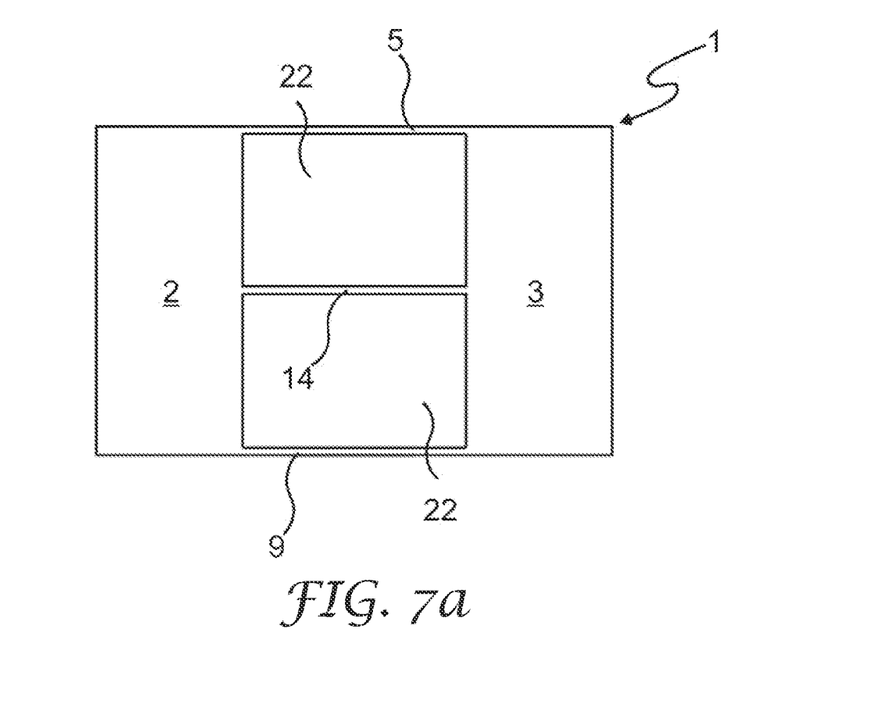
FIGS. 7a and 7b show the web according to FIG. 3 with two different widths of connection members after application of a pull force in longitudinal direction.
Figure 7B:
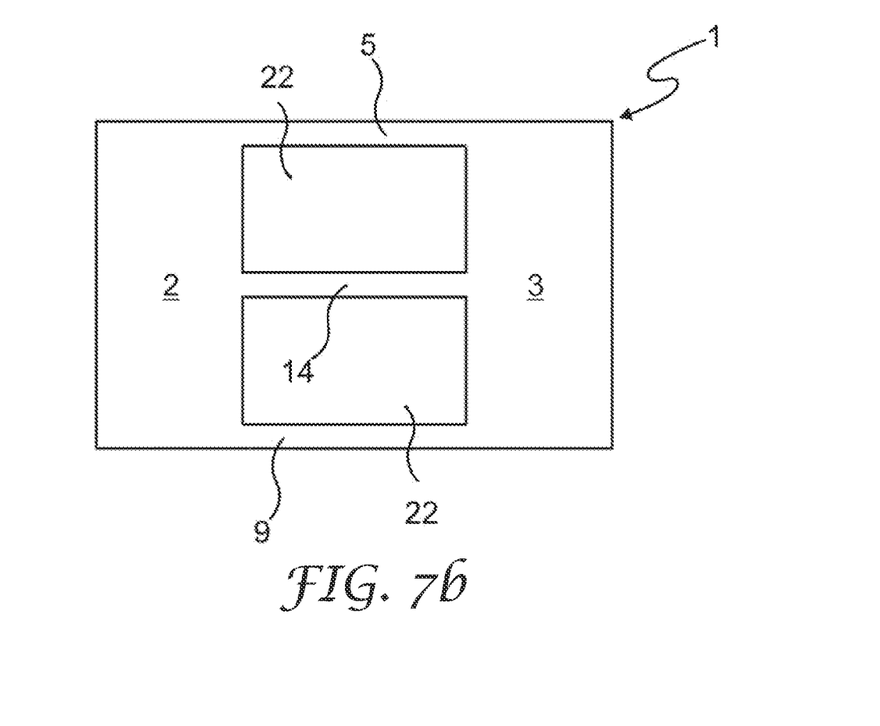

FIGS. 7a and 7b show the web according to FIG. 3 with two different widths of connection members 5, 9, 14 after application of a pull force in longitudinal direction of the web. As can be seen from these two figures, the different widths of connection members 5, 9, 14 yields holes 22 of different width between the adjacent tabs 2, 3.

Figure 8:
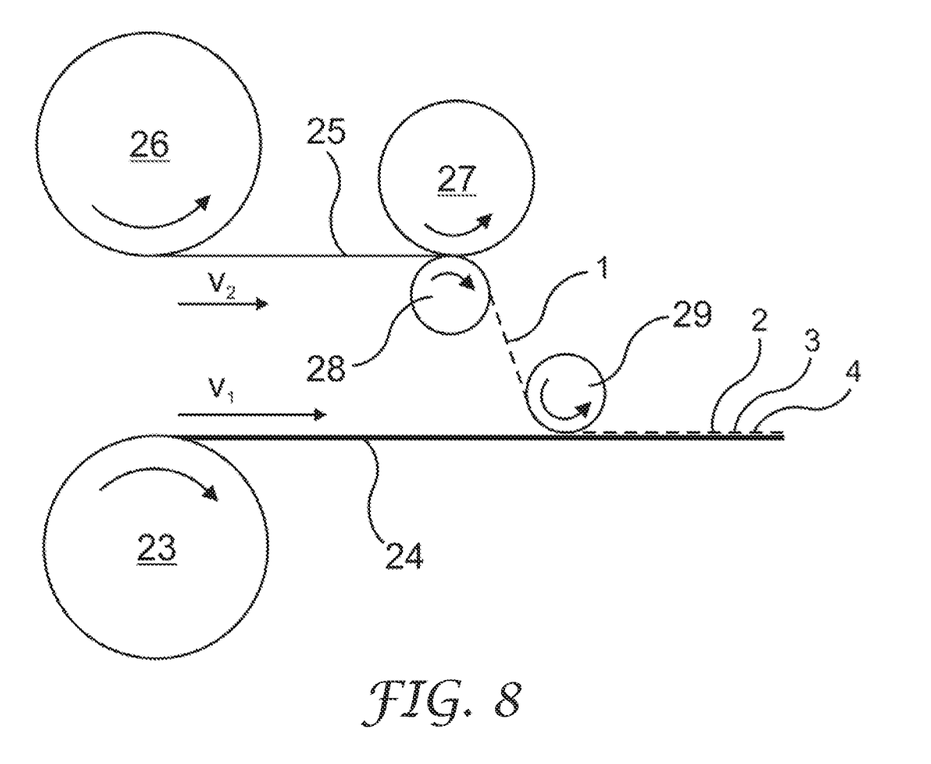
FIG. 8 shows a system for the fabrication of an elongate continuous material web and applying the web to a substrate.

FIG. 8 shows a system for the fabrication of an elongate continuous material web 1. The system comprises a roll 23, from which a hygiene article web 24 is provided with a transport velocity v1. Parallel to the hygiene article web 24, a raw material web 25 is provided from a roll 26 with a transport velocity v2, which is smaller than v1 as indicated by two straight arrows of different length.

The raw material web 25 is transported to a cutting cylinder 27, which cuts the incisions 6, 7, 8, 10, 11, 12, 15, 16, 17 into the web 1 and the perforation lines 20, 21 alongside the edges of the web 1 to form a plurality of adjacent tabs 2, 3, 4 arranged in the longitudinal direction of the web 1. During the cutting, the web 1 is pressed against the cutting cylinder 27 with a pressure roll 28.

The web 1 is transported to an applicator roll 29 with which the tabs 2, 3, 4 of the web 1 are adhered to the hygiene article web 24. Between the cutting cylinder 27 and the applicator roll 29, the transport velocity of the web 1 is higher than the transport velocity upstream of the cutting cylinder 27 so that the extendable connection members 5, 9, 14 are extended and the tabs 2, 3, 4 are spaced apart. The velocity increase at the cutting cylinder 27 is adjusted in such a way that the extendable connection members 5, 9, 14 are fully extended without rupturing them. Typically, the transport velocity downstream the cutting cylinder 27 is in the range of or equal to the transport velocity of the hygiene article web 24, i.e. v1. However, it is possible as well to increase the transport velocity at the applicator roll 29.

After the tabs 2, 3, 4 are adhered to the hygiene article web 15, the perforation lines 20, 21 are torn and the extensible connection members 5, 9 as well as slender edge areas from the tabs 2, 3, 4 are removed to yield single tabs 2, 3, 4 on the hygiene article web 24. The hygiene article web 24 can be cut afterwards in order to yield separate products (not shown in FIG. 8), like diapers for example, in which each diaper is provided with a predefined number of tabs 2, 3, 4.

Selected Embodiments of the Disclosure

In a first embodiment, the present disclosure provides an elongate continuous material web (1) comprising a plurality of adjacent tabs (2, 3, 4) arranged in a longitudinal direction of the web, wherein connection regions (A) are provided between adjacent tabs (2, 3, 4) comprising incisions (6, 7, 8, 10, 11, 12, 15, 16, 17) that extend in a transverse direction of the web, wherein each connection region (A) comprises three or more incisions (6, 7, 8, 10, 11, 12, 15, 16, 17) that extend in the transverse direction of the web and are arranged in such a manner that at least one extensible connection member (5, 9, 14) is formed, which is extensible in the longitudinal direction of the web, wherein at least one incision forms a side incision (8) that travels through one longitudinal edge of the web, and at least one incision forms a further side incision (11) that travels through the other longitudinal edge of the web.

In a second embodiment, the present disclosure provides the web according to the first embodiment, wherein at least one of the connection regions (A) consists of one single connection member (5) that comprises at least three adjacent incisions (6, 7, 8), each extending through one longitudinal edge of the web to almost the opposing longitudinal edge in alternating manner.

In a third embodiment, the present disclosure provides the web according to the first or second embodiment, wherein at least one of the connection regions (A) consists of two connection members (5, 9), arranged side by side in the transverse direction of the web, and separated from each other by a separating incision (13) that extends in the lengthwise direction of the web, wherein each extensible connection member (5, 9) comprises at least three incisions (6, 7, 8, 10, 11, 12) which extend in alternating manner from the separating incision (13) to almost one longitudinal edge of the web and through said longitudinal edge to almost the separating incision (13), wherein especially the side incisions (8, 11) are embraced by the other incisions (6, 7, 10, 12), if an uneven number of incisions (6, 7, 8, 10, 11, 12, 15, 16, 17) is present in the connection member (5, 9), respectively.

In a fourth embodiment, the present disclosure provides the web according to the third embodiment, wherein the two connection members (5, 9) are arranged to each other in an angled manner.

In a fifth embodiment, the present disclosure provides the web according to any one of the first to fourth embodiments, wherein at least one of the connection regions (A) consists of three extensible connection members (5, 9, 14), arranged side by side in the transverse direction of the web, wherein the inner extensible connection member (14) is separated from the outer extensible connection members (5, 9) by separating incisions (13, 18) that extend in the lengthwise direction of the web, and the incisions (15, 16, 17) of the inner extensible connection member (14) extend from one of the separating incisions (13, 18) to almost the other in alternating manner, and wherein the outer extensible connection members (5, 9) comprise at least three adjacent incisions (6, 7, 8, 10, 11, 12) which extend in alternating manner from the separating incisions (13, 18) to almost one longitudinal edge of the web and through said edge to almost the separating incisions (13, 18), respectively, whereas especially the side incisions (8, 11) are embraced by the other incisions (6, 7, 10, 12), if an uneven number of incisions (6, 7, 8, 10, 11, 12, 15, 16, 17) is present in the connection member (5, 9), respectively.

In a sixth embodiment, the present disclosure provides the web according to any one of the first to fifth embodiments, wherein the incisions (6, 7, 8, 10, 11, 12, 15, 16, 17) of each extensible connection member (5, 9, 14) extend parallel to each other, respectively.

In a seventh embodiment, the present disclosure provides the web according to any one of the first to sixth embodiments, wherein the incisions (6, 7, 8, 10, 11, 12, 15, 16, 17) of each extensible connection member (5, 9, 14) are uniformly spaced from one another.

In an eighth embodiment, the present disclosure provides the web according to any one of the first to seventh embodiments, wherein the incisions (6, 7, 8, 10, 11, 12, 15, 16, 17) extend mostly perpendicular to the longitudinal direction of the web.

In a ninth embodiment, the present disclosure provides the web according to any one of the third to eighth embodiments, wherein the extensible connection members (5, 9, 14) of one connection region (A) are formed by the same number of adjacent incisions (6, 7, 8, 10, 11, 12, 15, 16, 17).

In a tenth embodiment, the present disclosure provides the web according to any one of the first to ninth embodiments, wherein at least one of the incisions, preferably at least one of the adjacent incisions (6, 7, 8, 10, 11, 12, 15, 16, 17) and/or the separating incisions (13, 18), is provided with a hole punching (19) at its end region.

In an eleventh embodiment, the present disclosure provides the web according to any one of the first to tenth embodiments, wherein at least one main surface of the web is at least partly provided with an adherent agent, especially chosen from hooks, loops, adhesives or mixtures thereof.

In a twelfth embodiment, the present disclosure provides the web according to any one of the first to eleventh embodiments, wherein the web is provided on one or both of its long sides with a line of weakness (20, 21), especially a perforation, extending in the longitudinal direction and travelling in such a way through the extensible connection member (5, 9) that if the line of weakness (20, 21) is broken, the extensible connection members (5, 9) are separated from their assigned tabs (2, 3, 4), wherein the line of weakness (20, 21) especially crosses those incisions (6, 7, 10, 12), which travel to almost the edges of the long sides of the web.

In a thirteenth embodiment, the present disclosure provides the web according to any one of the first to twelfth embodiments, wherein the continuous material web having incisions (6, 7, 8, 10, 11, 12, 15, 16, 17) is wound on a roll.

In a fourteenth embodiment, the present disclosure provides an elongate continuous material web (1) comprising a plurality of adjacent tabs (2, 3, 4) arranged in a longitudinal direction of the web, wherein between two tabs (2, 3, 4) at least one hole is present, wherein the holes are formed by extending a continuous material web (1) according to any one of the first to thirteenth embodiments in the longitudinal direction.

In a fifteenth embodiment, the present disclosure provides a method for producing an elongate continuous material web comprising a plurality of adjacent tabs (2, 3, 4) arranged in a longitudinal direction of the web, wherein connection regions (A) are provided between adjacent tabs (2, 3, 4) comprising incisions (6, 7, 8, 10, 11, 12, 15, 16, 17) that extend in a transverse direction of the web, wherein the method comprises the steps of forming each connection region (A) by arranging three or more incisions (6, 7, 8, 10, 11, 12, 15, 16, 17) that extend in the transverse direction of the web in such a manner that at least one extensible connection member (5, 9, 14) is formed that is extensible in the longitudinal direction of the web, wherein at least one incision forms a side incision (8) that travels through one longitudinal edge of the web, and at least one incision forms a further side incision (11) that travels through the other longitudinal edge of the web.

In a sixteenth embodiment, the present disclosure provides a method for manufacturing a tab (2, 3, 4), especially a fastening tape tab, a hook tab or the like, the method comprising the steps of the method for producing an elongate continuous material web according to embodiment 15 and further removing edge areas on one or both long sides of the web in such a way that the extensible connection members (5, 9) are separated from their assigned tabs (2, 3, 4).

In a seventeenth embodiment, the present disclosure provides a method for manufacturing an absorbent hygiene or sanitary product, especially a diaper or a sanitary napkin, the method comprising:

providing an elongate absorbent hygiene material web or prepared portions thereof;

providing a continuous material web according to any one of the first to thirteenth embodiments;

bringing the continuous material web into contact with the elongate absorbent hygiene material web in such a way that its tabs (2, 3, 4) are positioned at desired locations of the elongate absorbent hygiene material web;

attaching the tabs (2, 3, 4) at those areas; and, at the same time or thereafter, optionally removing at least the connection members (5, 9, 14) between the tabs.

In an eighteenth embodiment, the present disclosure provides the method according to the seventeenth embodiment, wherein before or simultaneously with the step of bringing the continuous material web into contact with the elongate absorbent hygiene material web, the feed velocity of the continuous material web is increased so that the extensible connection members (5, 9, 14) are stretched, preferably mostly fully stretched.

In a nineteenth embodiment, the present disclosure provides a cutting device, especially in the form of a cutting cylinder (27), for the fabrication of a continuous material web comprising a plurality of adjacent tabs (2, 3, 4) arranged in a longitudinal direction of the web, wherein connection regions (A) are provided between adjacent tabs (2, 3, 4) comprising incisions (6, 7, 8, 10, 11, 12, 15, 16, 17) that extend in a transverse direction of the web, wherein the cutting device comprises groups of blades and/or punching units, arranged in such a way as to form each connection region (A) by three or more incisions (6, 7, 8, 10, 11, 12, 15, 16, 17) that extend in the transverse direction of the web and are arranged in such a manner that at least one extensible connection member (5, 9, 14) is formed that is extensible in the longitudinal direction of the web, wherein said blades and/or punching units are arranged to provide at least one incision which forms a side incision (8) that travels through one longitudinal edge of the web, and at least one incision which forms a further side incision (11) that travels through the other longitudinal edge of the web.

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein.

What is claimed is:

1. An elongate continuous material web comprising a plurality of adjacent tabs arranged in a longitudinal direction of the web and connection regions between adjacent tabs, wherein at least one main surface of the web is at least partly provided with an adherent agent selected from the group consisting of hooks, loops, adhesives, and mixtures thereof, wherein each connection region comprises at least three incisions that extend in the transverse direction of the web and are arranged in a manner such that at least one extensible connection member, which is extensible in the longitudinal direction of the web, is formed, wherein at least one incision forms a side incision that travels through one longitudinal edge of the web, and wherein at least one incision forms a further side incision that travels through the other longitudinal edge of the web.

2. The web according to claim 1, wherein at least one of the connection regions comprises one single extensible connection member that comprises at least three adjacent incisions, each extending through one longitudinal edge of the web to almost the opposing longitudinal edge in alternating manner.

3. An elongate continuous material web comprising a plurality of adjacent tabs arranged in a longitudinal direction of the web and connection regions between adjacent tabs, wherein each connection region comprises at least three incisions that extend in the transverse direction of the web and are arranged in a manner such that at least one extensible connection member, which is extensible in the longitudinal direction of the web, is formed, wherein at least one incision forms a side incision that travels through one longitudinal edge of the web, wherein at least one incision forms a further side incision that travels through the other longitudinal edge of the web, wherein at least one of the connection regions comprises two of the extensible connection members arranged side by side in the transverse direction of the web and separated from each other by a separating incision that extends in the lengthwise direction of the web, wherein each of the two extensible connection members comprises at least three incisions that extend in alternating manner from the separating incision to almost one longitudinal edge of the web and through said longitudinal edge to almost the separating incision.

4. The web according to claim 3, wherein an uneven number of incisions is present in each extensible connection member, and wherein the side incisions are positioned between the other incisions.

5. The web according to claim 3, wherein the two extensible connection members are arranged in an angled manner with respect to each other.

6. An elongate continuous material web comprising a plurality of adjacent tabs arranged in a longitudinal direction of the web and connection regions between adjacent tabs, wherein each connection region comprises at least three incisions that extend in the transverse direction of the web and are arranged in a manner such that at least one extensible connection member, which is extensible in the longitudinal direction of the web, is formed, wherein at least one incision forms a side incision that travels through one longitudinal edge of the web, wherein at least one incision forms a further side incision that travels through the other longitudinal edge of the web, wherein at least one of the connection regions comprises three of the extensible connection members, one inner extensible connection member and two outer extensible connection members, arranged side by side in the transverse direction of the web, wherein the inner extensible connection member is separated from the two outer extensible connection members by separating incisions that extend in the lengthwise direction of the web, wherein the inner extensible connection member comprises at least three adjacent incisions that extend from one of the separating incisions to almost the other in alternating manner, and wherein the outer extensible connection members comprise at least three adjacent incisions which extend in alternating manner from the separating incisions to almost one longitudinal edge of the web and through said edge to almost the separating incisions.

7. The web according to claim 6, wherein an uneven number of incisions is present in each extensible connection member, and wherein the side incisions are positioned between the other incisions.

8. The web according to claim 6, wherein each of the three extensible connection members of one connection region are formed by the same number of adjacent incisions.

9. The web according to claim 1, wherein at least one of the incisions is provided with a hole punching at its end region.

10. The web according to claim 1, wherein the at least three incisions of each extensible connection member extend parallel to each other, or wherein the at least three incisions of each extensible connection member are uniformly spaced from one another.

11. The web according to claim 1, wherein the at least three incisions are substantially perpendicular to the longitudinal direction of the web.

12. The web according to claim 3, wherein at least one main surface of the web is at least partly provided with an adherent agent selected from the group consisting of hooks, loops, adhesives, and mixtures thereof.

13. The web according to claim 1, wherein the web is provided on one or both of its long sides with a line of weakness extending in the longitudinal direction and traveling in such a way through the extensible connection member that if the line of weakness is broken, the extensible connection members are separated from their adjacent tabs, wherein the line of weakness especially crosses those incisions, which travel to almost the edges of the long sides of the web.

14. The web according to claim 1, wherein the continuous material web is wound on a roll.

15. An elongate continuous material web comprising a plurality of adjacent tabs arranged in a longitudinal direction of the web, wherein between two adjacent tabs at least one hole is present, wherein the holes are formed by extending the continuous material web according to claim 1 in the longitudinal direction.

16. A method for producing the elongate continuous material web of claim 1, the method comprising forming each connection region by arranging at least three incisions that extend in the transverse direction of the web in such a manner that at least one extensible connection member is formed that is extensible in the longitudinal direction of the web, wherein at least one incision forms a side incision that travels through one longitudinal edge of the web, and at least one incision forms a further side incision that travels through the other longitudinal edge of the web.

17. The method for manufacturing a tab according to claim 16, further comprising removing edge areas on one or both long sides of the web in such a way that the extensible connection members are separated from their adjacent tabs.

18. A method for manufacturing an absorbent hygiene or sanitary product, the method comprising:
providing an elongate absorbent hygiene material web or prepared portions thereof;
providing a continuous material web according to claim 1;
bringing the continuous material web into contact with the elongate absorbent hygiene material web in such a way that its tabs are positioned at desired locations of the elongate absorbent hygiene material web;
attaching the tabs at those areas; and, at the same time or thereafter,
optionally removing at least the connection members between the tabs.

19. The method according to claim 17, wherein before or simultaneously with bringing the continuous material web into contact with the elongate absorbent hygiene material web, the feed velocity of the continuous material web is increased so that the extensible connection members are stretched.

20. The web according to claim 3, wherein at least one of the incisions is provided with a hole punching at its end region.

21. The web according to claim 3, wherein the at least three incisions are substantially perpendicular to the longitudinal direction of the web.

* * * * *